United States Patent
Schlachta-Fairchild et al.

(10) Patent No.: US 7,792,884 B2
(45) Date of Patent: Sep. 7, 2010

(54) SYSTEM AND METHOD FOR CONDUCTING TAILORED SEARCH

(75) Inventors: Loretta Schlachta-Fairchild, Frederick, MD (US); Victoria Elfrink, Groveport, OH (US)

(73) Assignee: iTelehealth, Inc., Frederick, MD (US)

( * ) Notice: Subject to any disclaimer, the term of this patent is extended or adjusted under 35 U.S.C. 154(b) by 59 days.

(21) Appl. No.: 11/440,800

(22) Filed: May 25, 2006

(65) Prior Publication Data

US 2006/0271561 A1    Nov. 30, 2006

Related U.S. Application Data

(60) Provisional application No. 60/684,687, filed on May 26, 2005.

(51) Int. Cl.
*G06F 17/30* (2006.01)
(52) U.S. Cl. .......... 707/999.001; 707/999.003; 707/705; 707/706; 707/769; 707/770
(58) Field of Classification Search ........... 707/3, 707/10, 705, 706, 769, 770, 999.001, 999.003
See application file for complete search history.

(56) References Cited

U.S. PATENT DOCUMENTS

| | | | | |
|---|---|---|---|---|
| 4,675,904 A | * | 6/1987 | Silverman | 704/203 |
| 5,535,382 A | * | 7/1996 | Ogawa | 707/5 |
| 5,594,897 A | * | 1/1997 | Goffman | 707/102 |
| 5,768,580 A | * | 6/1998 | Wical | 707/102 |
| 5,787,421 A | * | 7/1998 | Nomiyama | 707/5 |
| 5,794,236 A | * | 8/1998 | Mehrle | 707/5 |
| 5,966,712 A | * | 10/1999 | Sabatini et al. | 707/104.1 |
| 6,385,611 B1 | * | 5/2002 | Cardona | 707/6 |
| 6,591,238 B1 | * | 7/2003 | Silverman | 704/270 |
| 6,742,004 B2 | * | 5/2004 | Sabatini et al. | 707/104.1 |
| 6,925,608 B1 | * | 8/2005 | Neale et al. | 715/763 |
| 7,058,643 B2 | * | 6/2006 | Vailaya | 707/101 |
| 7,062,443 B2 | * | 6/2006 | Silverman et al. | 704/274 |
| 7,162,465 B2 | * | 1/2007 | Jenssen et al. | 707/1 |
| 7,548,917 B2 | * | 6/2009 | Nelson | 707/7 |
| 7,552,395 B2 | * | 6/2009 | Neale et al. | 715/763 |
| 2004/0267566 A1 | * | 12/2004 | Badgett et al. | 705/2 |
| 2005/0192953 A1 | * | 9/2005 | Neale et al. | 707/4 |
| 2009/0228481 A1 | * | 9/2009 | Neale et al. | 707/5 |

OTHER PUBLICATIONS

"Maintaining a catalog of manually-indexed, clinically oriented , www content", Hersh et al., pp. 1-5, Jan. 1999.*
Teaching a systematic search strategy improves litterature retrieval skills of pharmacy student, Kathryn et al, Apr. 1996, vol. 60.*
The art &Science of web based litterature search the MEDLINE, Sahu et al., Apr. 1996, vol. 60, issue 2.*

* cited by examiner

*Primary Examiner*—Jean M Corrielus
(74) *Attorney, Agent, or Firm*—Mary S. Webster; Nixon Peabody, LLP (57) ABSTRACT

The system provides for a web-based user-interactive interface for providing focused tailored searches from various available databases. The interface permits a user to select search terms of interest, and to choose a database from various available databases. The system then provides the user with customized resources as the search result. Selectable terms are presented to the user through the interface using non-technical language. The system optionally enables registered users to receive monthly updates on their preferred search terms and may also provide users with a list of resources available from various databases.

5 Claims, 5 Drawing Sheets

SYSTEM AND METHOD FOR CONDUCTING TAILORED SEARCH

RELATED APPLICATIONS

This application claims the benefit under 35 U.S.C. §119(e) of U.S. provisional patent application Ser. No. 60/684,687, filed 26 May 2005, which is incorporated herein by reference.

STATEMENT REGARDING FEDERALLY SPONSORED RESEARCH OR DEVELOPMENT

This invention was made with Government support under Contract No. N44MH22044 awarded by the National Institutes of Health. The Government may have certain rights to this invention.

FIELD OF THE INVENTION

The present invention relates to searching, indexing, and extracting tailored information from a database. More specifically, the invention relates to techniques for facilitating locating customized resources within various databases and viewing search results using resources such as the Internet. The invention also relates to creating and developing a method for correlating or translating consumer search terms with specific search terms, such as Medical Subject Headings (MeSH®) terms.

BACKGROUND OF THE INVENTION

Databases, particularly those accessible via the Internet, provide a vast repository of information. Often, these databases are difficult and time-consuming to search, particularly for the layperson seeking knowledge about a technical field, by using specific search terms and methods, such as an area of medicine.

There is a growing body of literature that further supports the enhanced quality of information produced by tailored searches. Recent consumer-based studies have linked health care decision-making patterns with tailored information delivered via the World Wide Web. Tailored information is more effective in providing consumer information and is preferred by patients. Academic libraries include a greater degree of tailored information in their databases. A need remains, however, for innovative techniques for extracting tailored information from databases, such as a system that provides for user-friendly search terms and methodologies capable of retrieving technically and clinically correct information.

SUMMARY OF THE INVENTION

The present invention provides innovative techniques for extracting information from a database. In one embodiment, the invention provides for an interactive web-based search and retrieval system. The system includes: (1) a method to develop the most targeted and specific terms within the domain of knowledge and existing within the language database; (2) a web-based interactive user interface with specific selectable search terms associated with a selected topic; and (3) a query processor that, in response to the receipt of a search query from a requestor to a selected database, (a) translates the selected search term or terms to the appropriate database terms, (b) searches various resources (such as, for example, various databases within the NLM database containing professional journals, books, citations, full text, video, audio, and images), and (c) retrieves the resources containing the search term or terms selected.

Another aspect of the present invention provides a method for translating non-technical search terms into MeSH® controlled vocabulary.

In a particular embodiment of the invention, the query processor generates for the user a results page that lists suicide prevention resources from the National Library of Medicine (NLM) database. More preferably, in one embodiment of the invention, a system is provided that can search all the various National Institutes of Health (NIH) and/or NLM databases in a single search.

Another embodiment of the present invention provides a method for assisting a user in finding suicide prevention resources online by: (1) receiving a query from the user by choosing one or more search terms; (2) identifying a set of resources available for suicide or suicide prevention that satisfy the query, within the NLM database; and (3) generating and returning to the user a search results page that lists the available NLM resources as identified with the database.

Another aspect of the invention allows searching the NLM database using search terms in various languages such as, for example, the Spanish language.

Another embodiment of the invention provides for registered users to receive customized updates from various NLM resources within a customized web page. For example, registered users may receive monthly updates via email from various NLM resources indicating the number of new resources available since their last search.

One embodiment of the present invention comprises a method for using consumer search terms in a proprietary searchable database comprising the steps of: (1) establishing a consumer search term in a field of medicine; (2) correlating the consumer search term with at least one proprietary search term; (3) saving the correlation in a database; (4) saving the consumer search terms within the database; (5) linking the consumer search terms with the proprietary search terms according to the correlating step within the database; (6) receiving a search request from a user; correlating the search request with at least one consumer search term within the database; and (7) providing the at least one consumer search term. The establishing step may further comprise reviewing literature in the field of medicine, reviewing research in the field of medicine, reviewing at least one web site with content in the field of medicine, reviewing a plurality of web sites with content in the field of medicine, consulting with a medical professional and/or consulting with a librarian. The proprietary searchable database may be a MeSH® searchable database and/or an NLM database. The proprietary search term may comprise MeSH® search terms. The providing step may also provide at least one consumer search term to an NLM database. Furthermore, the consumer terms may be in a non-English language such as, for example, Spanish, and the field of medicine may be suicide prevention.

Another embodiment of the present invention may comprise a method for using consumer search terms in a consumer searchable database comprising the steps of: (1) establishing a consumer search term in a field of medicine; (2) correlating the consumer search term with other consumer search terms; (3) saving the correlation in a database; (4) receiving a search request from a user; (5) correlating the search request with at least one consumer search term within the database; and (6) providing the at least one consumer search term.

The present invention may also comprise a method for assisting a user in finding suicide prevention resources online, comprising the steps of: (1) receiving a query from the user by choosing one or more non-technical search terms; (2) identifying a set of resources available for suicide or suicide prevention that satisfy the query, within a National Library of Medicine database; (3) generating and returning to the user a search results page which lists the available NLM resources/publications as identified in the identifying step; and (4) emailing updates to users. The users may be registered users.

Another embodiment of the present invention may comprise a method for assisting a user in finding medical resources online, comprising the steps of: (1) receiving a query from a user; (2) generating consumer search terms by correlating the query with consumer search terms; (3) querying the NLM database for resources satisfying the consumer search terms; (4) returning resources to the user that satisfy the consumer query; and (5) emailing updates to users. The users may be registered users.

One object of the present invention is to provide a system and process for extracting customized information from the National Library of Medicine database. In one specific embodiment of the invention, the customized information being extracted pertains to suicide prevention. In another preferred embodiment of the invention, a user can search all of the NIH and/or NLM databases with a single search.

BRIEF DESCRIPTION OF THE DRAWINGS

Some features and advantages of the invention are described with reference to the drawings of certain preferred embodiments, which are intended to illustrate and not to limit the invention.

DETAILED DESCRIPTION OF THE INVENTION

It should be understood that this invention is not limited to the particular methodology, protocols, etc., described herein and, as such, may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, a reference to a database may be a reference to one or more such databases, including equivalents thereof known to those skilled in the art unless the context of the reference clearly dictates otherwise.

All patents and other publications identified are incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical terms used herein have the same meaning as those commonly understood to one of ordinary skill in the art to which this invention pertains. Although any known methods, devices, and materials may be used in the practice or testing of the invention, the preferred methods, devices, and materials in this regard are described here. By way of example, the following terminology is used within this application and may be interpreted in the following manner. "Consumer search terms" would include, for example, terms used by a lay person to perhaps less efficiently or directly search on a particular topic rather than specialized or converted terms, such as, for example MeSH® terms. "Consumer searchable databases" would include, for example, those databases typically searched or searchable by lay persons and not requiring specialized terminology, search strategy, or other skills and inputs to manipulate or interrogate effectively and efficiently. "Tailored search" refers, for example, to the use of tailored or converted search terms, rather than, for example, consumer search terms, to more efficiently or directly obtain desired search results.

Briefly, one embodiment of the present invention is a method that allows a consumer to use consumer search terms in a proprietary searchable database. A user on a webpage may implement this method. Some databases use proprietary search terms that are foreign to the lay user. Although experts or repeat users may be familiar with the proprietary search terms and how they interrelate with the database, these terms may often be confusing to a layperson. As such, a layperson's ability to retrieve the most relevant information will likely be limited without the use of the aspects of the present invention. The method of this embodiment of the present invention involves the steps of establishing a consumer search term, correlating the consumer search term with at least one proprietary search term, and saving the correlation in a database. In another embodiment the correlation step may comprise a translation. The database may in one specific embodiment be a MeSH® searchable database or an NLM database. Likewise the proprietary search term may be a MeSH® search term or a proprietary search term in a field of medicine. The establishing step may comprise one or more of the following: reviewing literature in a field of medicine, reviewing research in a field of medicine, reviewing at least one web site with content in a field of medicine, reviewing a plurality of web sites with content in a field of medicine, consulting with a medical professional, and consulting with a librarian.

In another embodiment of the present invention, the aforementioned saving step includes the steps of saving the consumer search terms within the database and linking the consumer search terms with other consumer search terms according to the correlating step within the database. The method may also comprise the steps of receiving a search request from a user, correlating the search request with at least one consumer search term within the database, and providing the at least one consumer search term.

The present invention may also comprise the method of: (1) receiving a search request from a user; (2) correlating the search request into proprietary search terms such as, for example, MeSH® search terms; (3) forwarding these proprietary search terms to an associated database for searching; (4) receiving a result from the search; and (5) providing this result to the user. Specifically, the user may be inquiring about suicide prevention, for example. The user may input a search request, couched in consumer search terms. The received terms are translated and/or correlated into MeSH® search terms. Once correlated or translated, the terms are used in an NLM database to search for results to the users query. These results may then be forwarded back to the user.

The methods of the present invention may be implemented in a language other than English. For instance, the method may be implemented by a webpage that is in Spanish. In such an embodiment the present invention would correlate Spanish consumer search terms into the proprietary search terms, such as, for example, MeSH® search terms.

Furthermore, the embodiments of the present invention are not limited to a given field of research, or to any specific proprietary search terms or databases. The present invention may be used to search any database, in any field of inquiry.

The present invention may also provide a system or method with various features for assisting users in conducting online searches specific to a desired topic, for example suicide prevention or remote-location-based healthcare services, from various resources available from databases, such as those provided by the NLM. One feature of the invention involves a method for translating non-technical specific suicide terms into controlled vocabulary terms such as MeSH® vocabulary terms. The selected search terms are sent to the database of choice, e.g., an NLM database, and the results are displayed.

A specific embodiment of the invention provides a system whereby specific suicide prevention information can be accessed online from databases, such as the NLM databases, by first accessing a tailored search and retrieval interface. Using this interface to identify a specific role or factors associated with suicide prevention offers an efficient, user-friendly and customizable way to locate reliable resources outside of the website. Results from the searches are displayed clearly for printing, or linking to a particular resource. There is no limit to the number of times that a tailored search may be performed.

Creating such a web-based interface requires many possible steps. These steps can occur with any domain of knowledge, e.g., suicide, diabetes, cardiac disease, pediatrics, telehealth, etc. Many of these steps may occur well before any computer code is written or created. For example, the process may begin with a literature review of relevant literature and research. Relevant websites may also be reviewed. Particular clinicians and consultants familiar with the target topic may be consulted for advice in determining organization and layout of the website. Development of user interface search terms, and revisions of these search terms may be ongoing throughout this process, as is the development of higher-level associated categories and specific term organization. A tailored search page may then be designed, and revised as needed after, for example, receiving feedback from clinical consultants and/or medical librarians. Tailored search terms and formatting may be ultimately delivered to a technical team for implementation of search strategy.

An aspect of the present invention involves a method for identifying and displaying resources derived from various NLM databases in response to a query submitted by the user. Another feature of the invention involves methods for users to select search terms unique to suicide and suicide prevention, where the terms may then be translated to MeSH® controlled vocabulary.

Figure 1:
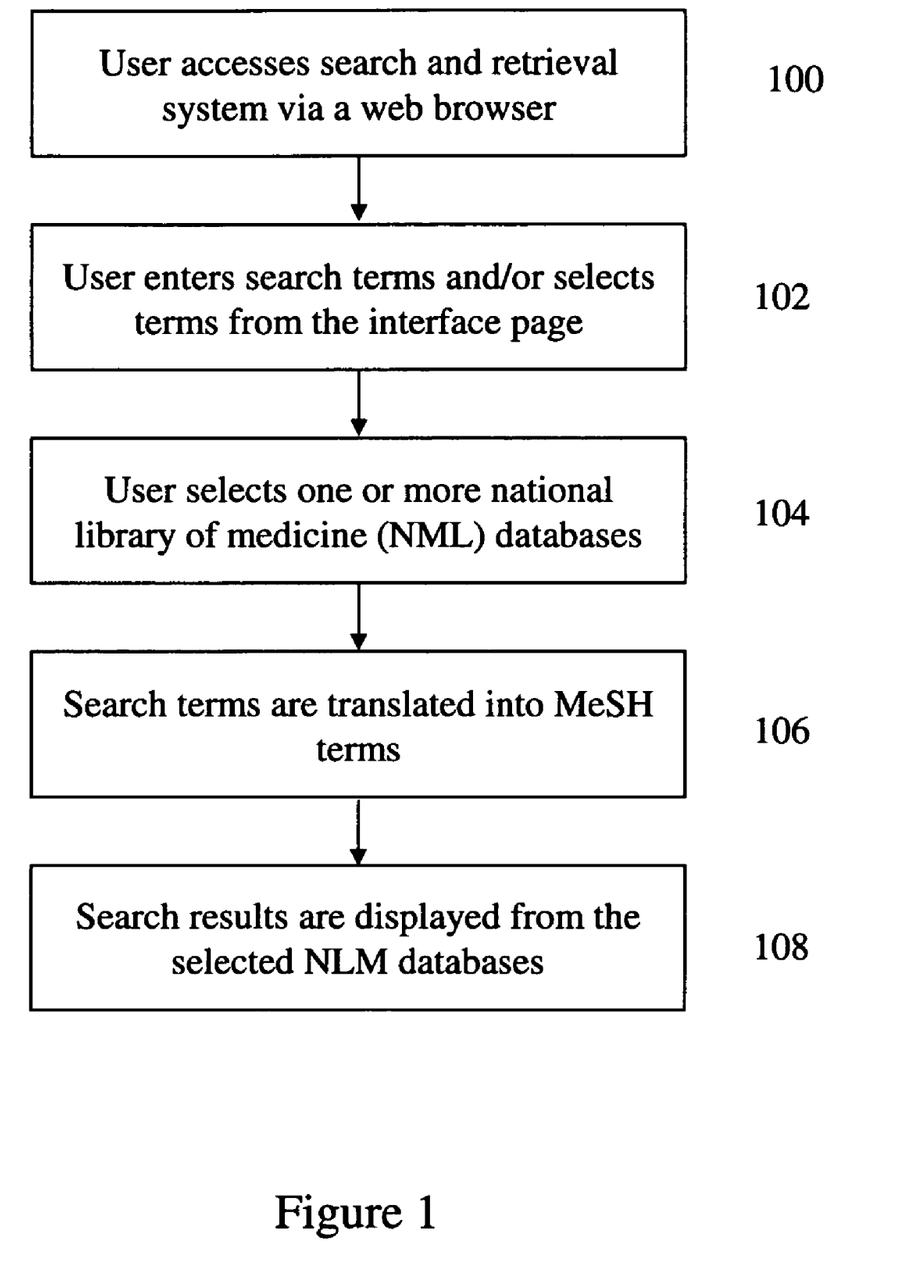
FIG. 1 illustrates a flow diagram of an example search and retrieval system of an embodiment of the present invention.

An example embodiment and implementation of the invention is described with reference to the drawings. FIG. 1 illustrates the flow of the search and retrieval system. The user accesses a search and retrieval system via a web browser 100, then enters and/or selects one or more search terms from a search interface page 102. The user selects the appropriate NLM database for searching needs by scrolling through and selecting from the options 104. There are seven currently existing NLM databases from which to choose. The system converts the search terms into MeSH® terms 106 and performs the appropriate search. The search results may then be provided to the user 108 and the user may scroll and/or browse through the results. The results may include citations, publications, journals, images, books, etc.

Specific search terms may include, for example, terms in various subheadings such as roles, factors, or strategies. For example, one may search by personal role of the user, such as adult, parent, adolescent. A professional role search terms may also be included, such as student, instructor, counselor of clergy member, or the like.

Some exemplary factors associated with the research topic may also be included as search terms. These may include the age, race, gender or religion of the research target, the behaviors associated with particular indications, the living or employment status of the research target. Associated factors may also include medical indications such as particular disorders or diseases, side-effects, symptoms, diagnoses or recent events that may be implicated in the target's current condition. Intervention strategies may also be included in search terms. These strategies may include, for example, level of care, medications, or other therapies.

The National Library of Medicine (NLM) manages a number of online medical databases that may be searched with embodiments of the present invention. For example, the embodiments of the present invention may search the following NLM databases: database of professional journals, database of consumer health information, database of books, audiovisual materials, etc, database of clinical research studies, database of online support organizations, database of full-text documents, and database of research on drug toxicological effects. Additional resources include those found on the internet.

The embodiments of the present invention may occur in languages other than English, such as, for example Spanish.

Figure 2:
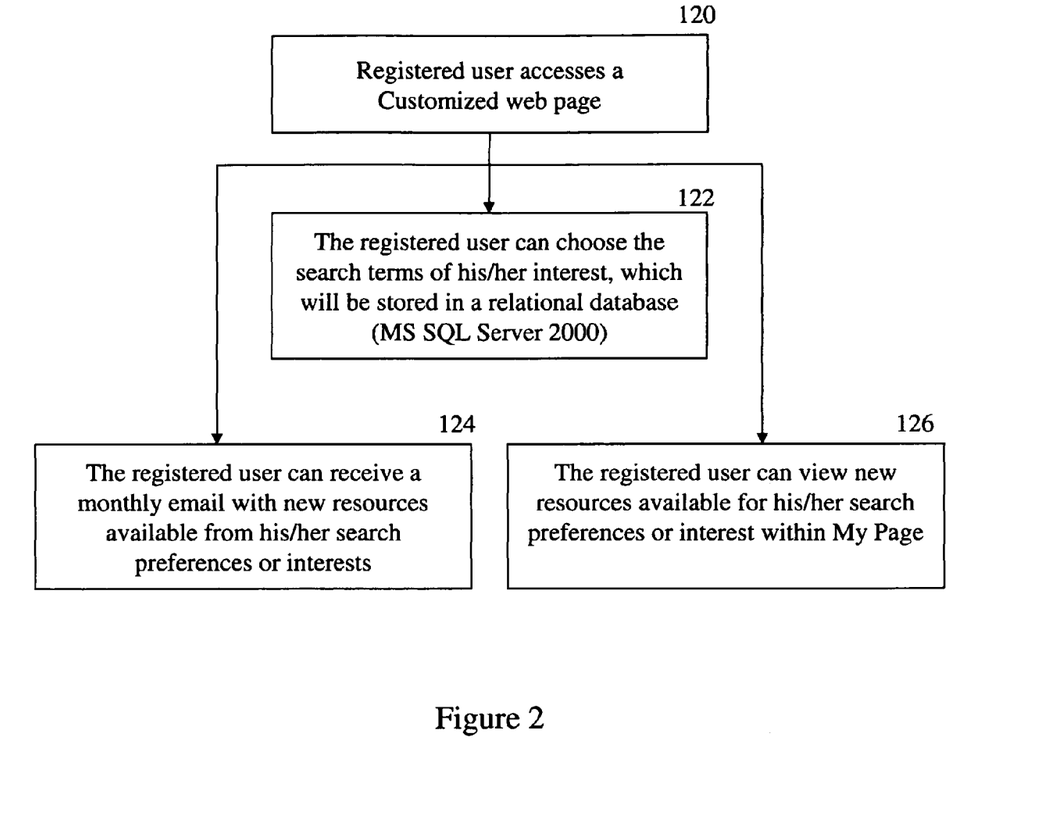
FIG. 2 illustrates an aspect of the invention whereby a user may be supplied with a customized page (e.g., My Page) when the user is interested in specific search results.

FIG. 2 illustrates the flow within "My Page," a customized page for registered users. By accessing this customized page, a registered user has the capability of choosing their preferred search terms, or set other various user options. The registered users are able to view the number of new resources available to them in their area of interest by clicking on the GO button. This link can take them to the number of available resources. If interested, the users can receive a monthly email providing them with number of resources available to them since their last visit to the site.

In one specific embodiment a relational database is utilized with, for example, ninety-eight search terms. The search terms table is linked to the users table, in which information for registered users is stored.

Figure 3:
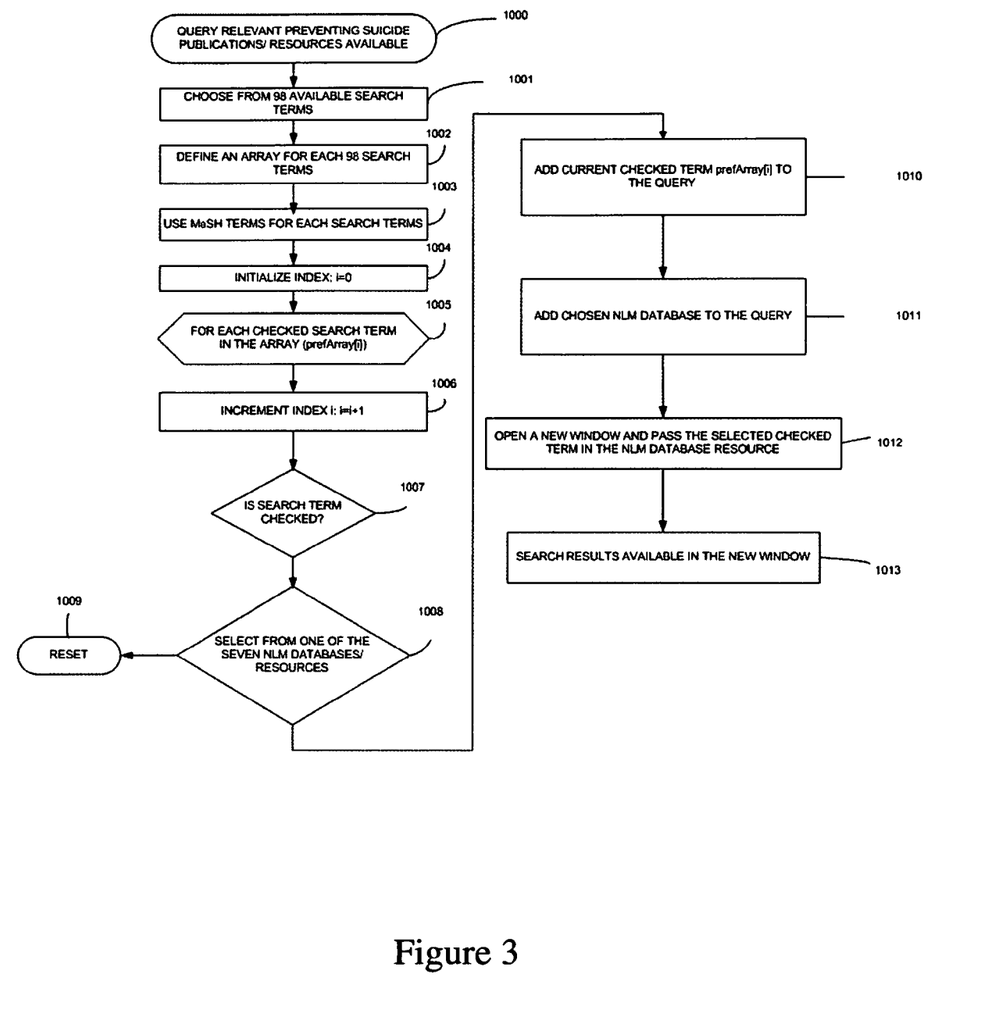
FIG. 3 presents a high level flow diagram of an exemplary method of the present invention that may be used to extract results from queries submitted to various NLM database resources.

FIG. 3 is a high-level flow diagram of an exemplary method 1000 which can be used to extract information by querying various NLM databases on preventing suicide resources. The end user can choose from ninety-eight various search terms 1001. An array is defined from the ninety-eight search terms 1002. Each search term is translated to a MeSH® term 1003. An index is then initialized with value 1004, then passes the value to the array 1005 and adds one to the value of this index 1006.

If a search term is checked 1007, the user can choose from seven currently available NLM resources/databases 1008. The user can reset his search at this point 1009. Otherwise the checked search terms the end user has chosen are added to the query 1010. The desired NLM resource/database is then added to query 1011. The selected search using MeSH® terms is then passed to the desired NLM resource 1012. The results are presented in a new window 1013.

Figure 4:
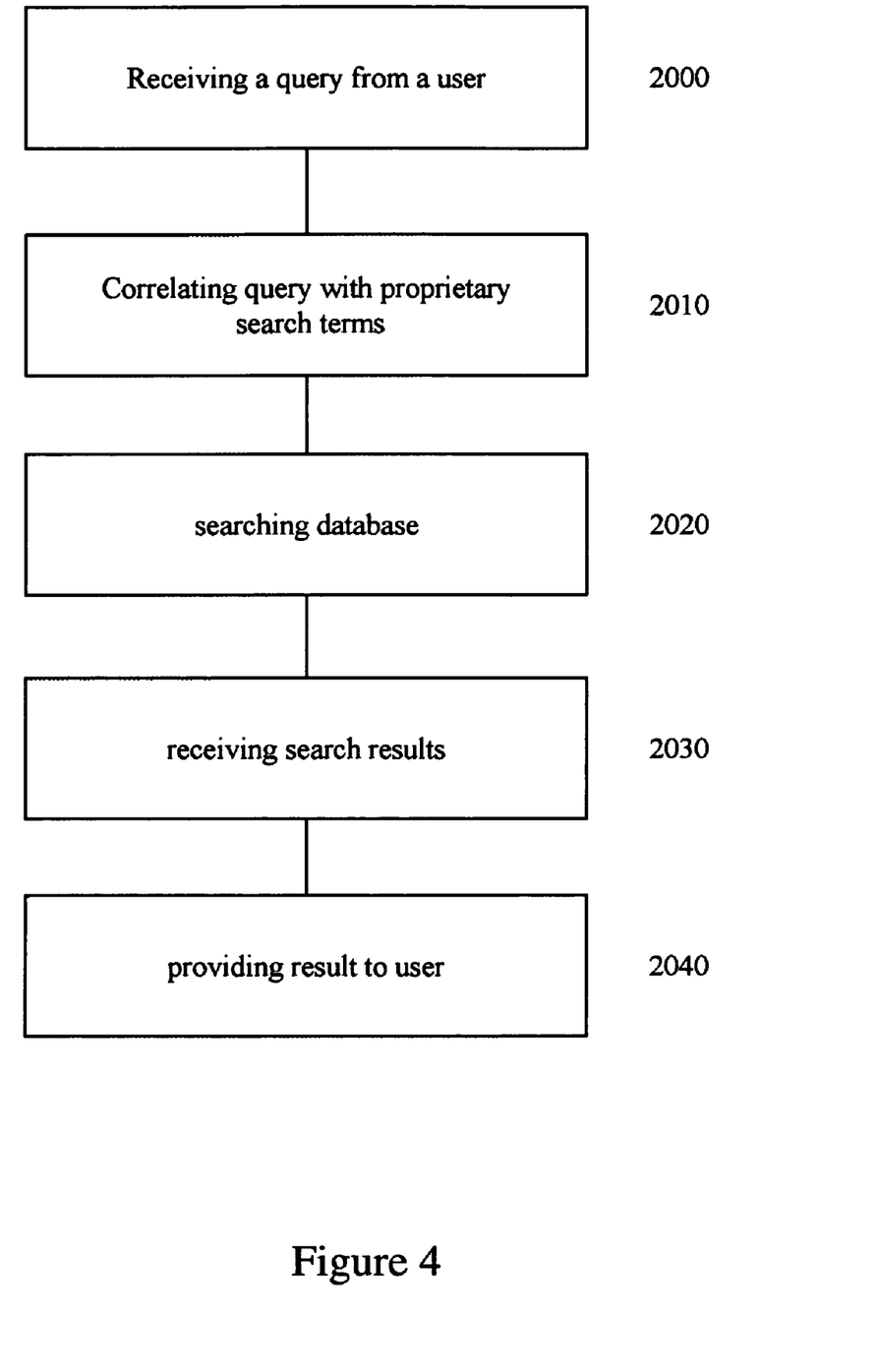
FIG. 4 presents a flow diagram of one embodiment of the present invention.

FIG. 4 is a flow chart of another embodiment of the present invention. This chart represents the flow of information when a query is received from a user. A search query is first received from a user 2000 that comprises consumer search terms. These terms are then correlated with proprietary search terms 2010. A search of the database with these proprietary terms 2020 is used. Results are then returned from the database 2030 which are then provided to the user 2040.

Another aspect of the present invention is a method for using consumer search terms in a MeSH® searchable database. MeSH® searchable databases are often difficult for a layperson to search. For example, the consumer search terms a layperson may use to search a database may not correlate well with appropriate MeSH® terms. These consumer search terms may make sense to the searcher, but may not return the most desired tailored results. This limitation makes it difficult for the layperson to search a MeSH® searchable database and receive search results that they seek. Translating consumer search terms into MeSH® terms or correlating consumer search terms with MeSH® terms prior to searching a database may provide a user with a more tailored search and provide them with more applicable results.

This method may comprise the steps of establishing a consumer search term in a field of medicine for a specific search. This step may be accomplished, for example, by reviewing related literature, consulting with medical professionals, consulting with a research librarian, viewing websites, and consulting with clinicians and consultants in a field of interest. Next the consumer search terms may be correlated with or translated into MeSH® search terms. For example, by noting the MeSH® search terms needed to return results related to the specific consumer search terms established in the previous step, a correlation or translation may be established. Finally, the correlation may be saved in a database. This saving step may include saving the consumer and MeSH® terms within a database and linking related terms according to the correlation or translation.

Figure 5:
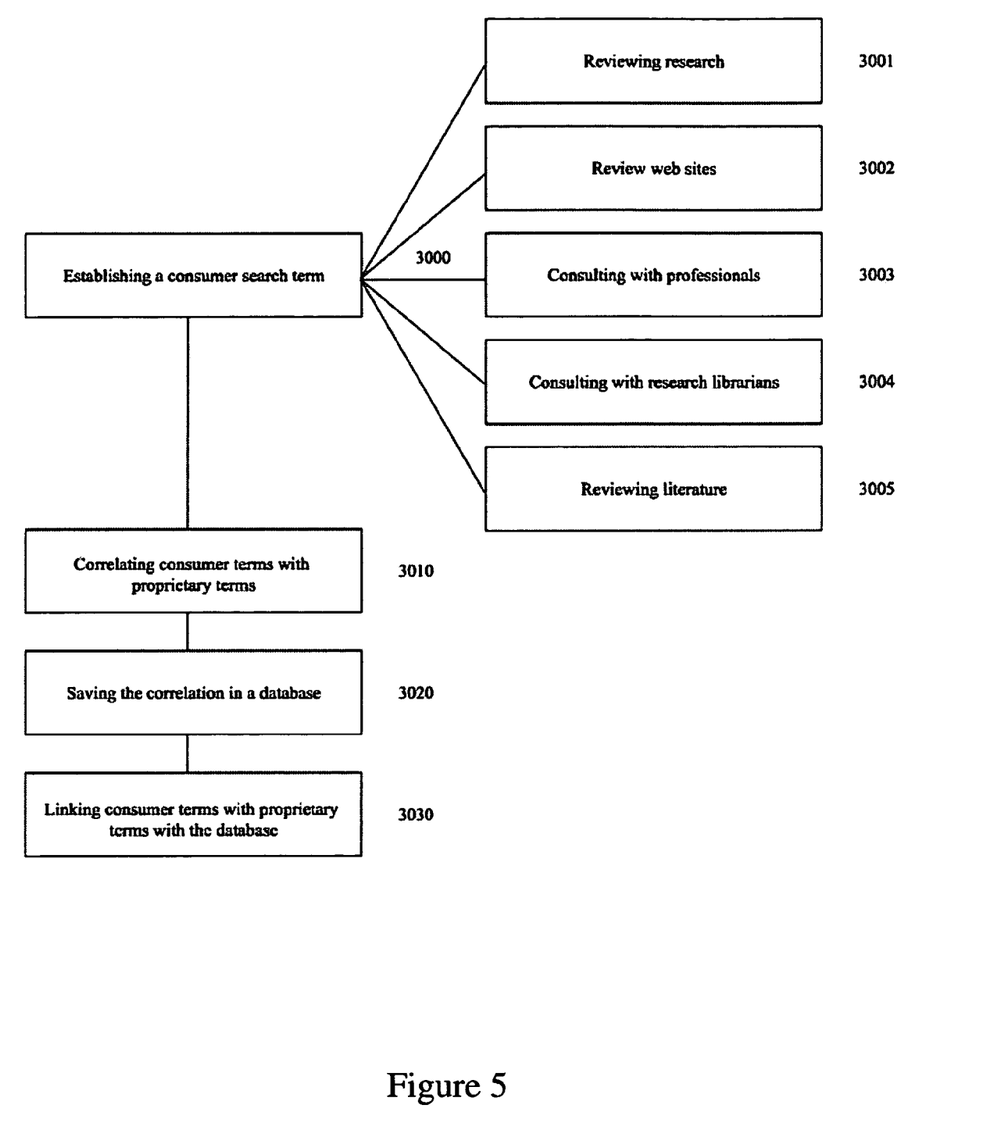
FIG. 5 presents a flow diagram of another embodiment of the present invention.

FIG. 5 presents a flow chart showing possible steps used to establish search terms and create a database of correlated consumer and proprietary search terms. First consumer search terms are established 3000. This may be accomplished in a number of different ways including reviewing research in the given field 3001, reviewing web sites 3002, consulting with professionals 3003, consulting with librarians 3004, and reviewing literature in a given field 3005. These consumer search terms are then correlated with proprietary search terms 3010. This step may be accomplished manually. This correlation is then saved into a database 3020 where the consumer and proprietary terms are linked together 3030.

The methods of the present invention may allow a system to receive a search request using consumer search terms, correlate this search request with associated MeSH® search terms, and then provide these MeSH® search terms to a MeSH® searchable database. For example, the system may receive consumer search terms in the field of suicide prevention, correlate these consumer search terms into MeSH® search terms, and then present them to an NLM database for searching. The results from this search may then be passed back to the user. Using this method, users may search MeSH® searchable databases with familiar consumer search terms and receive optimal results.

EXAMPLE

Creation of a Suicide Prevention Web Site

In a particular embodiment of the invention, utilizing one or more of the various aspects or embodiments of the method described above, a system was provided for extracting customized information from the NLM databases pertaining to the creation of the Prevent Suicide Network (PSN) web site. An overview of this process is depicted in FIG. 5.

Personnel conducted a literature review of suicide prevention and mental health literature and research into suicide, including risk factors (some of which are discussed above), interventions, and prevention techniques. Personnel also reviewed existing web sites dedicated or relating to suicide and suicide prevention. Personnel consulted with health clinicians and suicidology consultants to determine organization and layout.

The development of user interface search terms was based on the knowledge gained throughout the review and consultation processes, and included several rounds of internal review and revision of terms. As the search terms evolved, so did the development of higher level associated categories and specific term organization.

A draft of the tailored search page was then created, followed by internal review and revision of the search page. This was followed by external review and evaluation of tailored search page by clinical consultants and medical librarians.

This revision and review process continued (totaling five revisions) culminating in a final version that was delivered to a technical team for implementation of search strategy. Once implemented, one search strategy could be employed to search the all NIH databases.

A version of this search system, an embodiment of the present invention, is presently available at a .com Web site entitled "preventingsuicide" from which the user may access the Tailored Search Page that accesses the NLM as described herein. When the user accesses this site, they may 'click' in a Conduct a Tailored Search lick, which directs the user to the Tailored Search Page. At this page, the user simply checks the box of the appropriate search terms and may conduct a search of the NLM libraries. This search is available in either English or Spanish languages.

Specific suicide prevention search terms may include, for example, terms in various subheadings such as roles, factors or intervention strategies. For example, one may search by personal role selecting the search term for adult, family and friends, parent, survivor of suicide attempt, or teen and young adult. Professional role search terms, may include, for example, AOD counselor, clergy member, corrections worker, counselor, social worker, crisis center worker, educator, employer, first responder, geriatric specialist, justice system professional, media professional, nurse, physician, policy maker, psychologist, psychiatrist, public or state health professional, researcher, school clinician, or the like.

Some exemplary factors associated with suicide prevention may also be included as search terms. These factors may include age: children, adolescents, early adults, middle adults, older adults and/or late adults. The associated may also, for example, include behaviors such as perfectionism, previous suicide attempt, problem solving ability, and/or social isolation. The factors may also include search terms for unemployed, employed, male, female, married, divorced, single parent never married, single parent, widowed and/or current medications.

Mental health disorders may also be included in the search terms as an associated factor. Disorders may include: anxiety, depressive, mental health, psychotic, schizophrenia, panic attacks, personality disorder, borderline personality disorder, and/pr substance abuse dependencies. It may also include race and ethnicity such as: African American, Alaskan Native, American Indian, native American, Asian American, Biracial, Multiracial, Caucasian, Culture, Latino, Hispanic, and/or Pacific Islander. Religion may also be an associated factor search term and may include Buddhism, Catholicism, Hinduism, Islam, Judaism, and/or Protestantism. The associated factors may also include stressors/life experiences such as, for example, chronic illness, HIV or AIDS diagnosis, family dysfunction, feelings of hopelessness, gay, lesbian, bisexual, sexual orientation, interpersonal relationships, immigrant, life stress, physical abuse, physical health, refuge, and/or sexual abuse.

Intervention strategies may also be included in suicide prevention search terms. These strategies may include, for example, level of care including day treatment, impatient/full hospitalization, out patient treatment, partial hospitalization, residential treatment, and/or half-way house. Medications may also be part of intervention strategies including, for example, anticonvulsant, antidepressant, antipsychotic, anxiolytic, and/or mood stabilizer drugs. Various therapies may also be included in the intervention strategies such as, for example, behavior therapy, brief therapy, cognitive behavioral therapy (CBT), dialectical behavior therapy (DBT), electroconvulsive therapy, interpersonal therapy, and/or psychodynamic/insight-oriented therapy.

The National Library of Medicine (NLM) manages a number of online medical databases that may be searched with embodiments of the present invention. For example, the embodiments of the present invention may search the following NLM databases: database of professional journals, database of consumer health information, database of books, audiovisual materials, etc, database of clinical research studies, database of online support organizations, database of full-text documents, and database of research on drug toxicological effects.

In this fashion, the lay person has access to the highest levels of scholarship in the Database of Professional Journals (PubMed). Alternatively, if the user chooses a different database, another browser window with additional resources opens for the user.

Although the invention has been particularly shown and described with reference to the various embodiments provided above, modifications of the above described modes for carrying out the invention that are obvious to those of ordinary skill in the related arts are intended to be within the scope of the appended claims.

What is claimed is:

1. A method for assisting a user in finding suicide prevention resources online, wherein the user employs an interactive web-based search and retrieval system, comprising the steps of:
   receiving a query, including at least one search term, from the user;
   presenting the user with at least one proprietary term correlated to the at least one search term;
   updating the query to include the search term and any proprietary terms selected by the user;
   identifying, within at least one National Library of Medicine (NLM) database-selected by the user, a set of NLM resources/publications that satisfy the query; and
   generating and returning to the user a search results page that lists the available NLM resources/publications identified in said identifying step,
   wherein the proprietary search term relates to at least one of a personal role, a professional role, an intervention strategy, age, exemplary factors, behaviors, mental health disorders, race, religion, or stressors,
   wherein the personal role terms include at least one of adult, family, friend, parent, survivor of suicide attempt, teenager, and young adult,
   wherein the professional role terms include at least one of AOD counselor, clergy member, corrections worker, counselor, social worker, crisis center worker, educator, employer, first responder, geriatric specialist, justice system professional, media professional, nurse, physician, policy maker, psychologist, psychiatrist, public or state health professional, researcher and school clinician,
   wherein the intervention strategy terms include at least one of level of care including day treatment, impatient/full hospitalization, out patient treatment, partial hospitalization, residential treatment, and half-way house,
   wherein the terms for age include at least one of children, adolescents, early adults, middle adults, and late adults,
   wherein the terms for exemplary factors include at least one of unemployed, employed, male, female, married, divorced, single parent never married, widowed, and current medications,
   wherein the terms for behaviors include at least one of perfectionism, previous suicide attempt, problem solving ability, and social isolation,
   wherein the terms for mental health disorders include at least one of anxiety, depression, psychotic, schizophrenia, panic attacks, personality disorder, borderline personality disorder, and substance abuse dependencies,
   wherein the terms for race include at least one of African American, Alaskan Native, American Indian, native American, Biracial, Multiracial, Caucasian, Culture, Latino, Hispanic, and Pacific Islander,
   wherein the terms for religion include at least one of Buddhism, Catholicism, Hinduism, Islam, Judaism, and Protestantism, and
   wherein the terms for stressors include at least one of chronic illness, HIV, AIDS, family dysfunction, feelings of hopelessness, gay, lesbian, bisexual, sexual orientation, interpersonal relationships, immigrant, life stress, physical abuse, physical health, refuge, and sexual abuse.

2. The method of claim 1, further comprising a step of emailing updates to users.

3. The method of claim 2, wherein the user is a registered user.

4. A system for assisting a user in finding suicide prevention resources online, wherein the user employs an interactive web-based search and retrieval system, comprising:
   means for receiving a query, including at least one search term, from the user;
   means for presenting the user with at least one proprietary term correlated to the at least one search term;
   means for updating the query to include the search term and any proprietary terms selected by the user;
   means for identifying, within at least one National Library of Medicine database selected by the user, a set of NLM resources/publications that satisfy the query; and
   means for generating and returning to the user a search results page that lists the available NLM resources/publications identified in said identifying step,
   wherein the proprietary search term relates to at least one of a personal role, professional role, an intervention strategy, age, exemplary factors, behaviors, mental health disorders, race, religion, or stressors, wherein the personal role terms include at least one of adult, family, friend, parent, survivor of suicide attempt, teenager, and young adult, wherein the professional role terms include at least one of AOD counselor, clergy member, corrections worker, counselor, social worker, crisis center worker, educator, employer, first responder, geriatric specialist, justice system professional, media professional, nurse, physician, policy maker, psychologist, psychiatrist, public or state health professional, researcher and school clinician, wherein the intervention strategy terms include at least one of level of care including day treatment, impatient/full hospitalization, out patient treatment, partial hospitalization, residential treatment, and half-way house, wherein the terms for age include at least one of children, adolescents, early adults, middle adults, and late adults, wherein the terms for exemplary factors include at least one of unemployed, employed, male, female, married, divorced, single parent never married, widowed, and current medications, wherein the terms for behaviors include at least one of perfectionism, previous suicide attempt, problem solving ability, and social isolation, wherein the terms for mental health disorders include at least one of anxiety, depression, psychotic, schizophrenia, panic attacks, personality disorder, borderline personality disorder, and substance abuse dependencies, wherein the terms for race include at least one of African American, Alaskan Native, American Indian, native American, Biracial, Multiracial, Caucasian, Culture, Latino, Hispanic, and Pacific Islander, wherein the terms for religion include at least one of Buddhism, Catholicism, Hinduism, Islam, Judaism, and Protestantism, and wherein the terms for stressors include at least one of chronic illness, HIV, AIDS, family dysfunction, feelings of hopelessness, gay, lesbian, bisexual, sexual orientation, interpersonal relationships, immigrant, life stress, physical abuse, physical health, refuge, and sexual abuse.

5. A method for assisting a user in finding medical resources online, wherein the user employs an interactive web-based search and retrieval system, comprising the steps of:

receiving a query, including at least one disease specific search term, from the user;

presenting the user with at least one proprietary term correlated to the at least one search term;

updating the query to include the search term and any proprietary terms selected by the user;

identifying, within at least one National Library of Medicine (NLM) database-selected by the user, a set of NLM resources/publications that satisfy the query; and generating and returning to the user a search results page that lists the available NLM resources/publications identified in said identifying step, wherein the proprietary search term relates to at least one of a personal role, a professional role, an intervention strategy, age, exemplary factors, behaviors, mental health disorders, race, religion, or stressors, wherein the personal role terms include at least one of adult, family, friend, parent, survivor of suicide attempt, teenager, and young adult, wherein the professional role terms include at least one of AOD counselor, clergy member, corrections worker, counselor, social worker, crisis center worker, educator, employer, first responder, geriatric specialist, justice system professional, media professional, nurse, physician, policy maker, psychologist, psychiatrist, public or state health professional, researcher and school clinician, wherein the intervention strategy terms include at least one of level of care including day treatment, impatient/full hospitalization, out patient treatment, partial hospitalization, residential treatment, and half-way house, wherein the terms for age include at least one of children, adolescents, early adults, middle adults, and late adults, wherein the terms for exemplary factors include at least one of unemployed, employed, male, female, married, divorced, single parent never married, widowed, and current medications, wherein the terms for behaviors include at least one of perfectionism, previous suicide attempt, problem solving ability, and social isolation, wherein the terms for mental health disorders include at least one of anxiety, depression, psychotic, schizophrenia, panic attacks, personality disorder, borderline personality disorder, and substance abuse dependencies, wherein the terms for race include at least one of African American, Alaskan Native, American Indian, native American, Biracial, Multiracial, Caucasian, Culture, Latino, Hispanic, and Pacific Islander, wherein the terms for religion include at least one of Buddhism, Catholicism, Hinduism, Islam, Judaism, and Protestantism, and wherein the terms for stressors include at least one of chronic illness, HIV, AIDS, family dysfunction, feelings of hopelessness, gay, lesbian, bisexual, sexual orientation, interpersonal relationships, immigrant, life stress, physical abuse, physical health, refuge, and sexual abuse.

* * * * *